United States Patent [19]

Komissarova et al.

[11] Patent Number: 5,798,371

[45] Date of Patent: Aug. 25, 1998

[54] PHARMACEUTICAL COMPOSITION ENDOWED WITH AN ANTIALCOHOLIC AND NOOTROPIC EFFECT

[76] Inventors: Irina Alexeevna Komissarova, ulitsa Medikov, 24, kv.47; Julia Vasilievna Gudkova, Zelenograd, korpus 165, kv. 131; Tatyana Dmitrievna Soldatenkova, Pokrovsky bulvar, 14/5, kv.73; Tatyana Tikhonovna Kondrashova, ul.Severodvinskaya, 9, kv.305, all of Moscow; Natalya Mikhailovna Burbenskaya, Ozersky r-n, p/o Sennitsy, Moskovskaya obl., all of Russian Federation

[21] Appl. No.: 704,745

[22] PCT Filed: Jan. 4, 1996

[86] PCT No.: PCT/RU96/00006

§ 371 Date: Sep. 6, 1996

§ 102(e) Date: Sep. 6, 1996

[87] PCT Pub. No.: WO96/21446

PCT Pub. Date: Jul. 18, 1996

[30] Foreign Application Priority Data

Jan. 13, 1995 [RU] Russian Federation ............. 95100307

[51] Int. Cl.$^6$ ...................... A61K 31/44; A61K 31/195
[52] U.S. Cl. .................. 514/345; 514/561; 514/811
[58] Field of Search .................. 514/561, 345, 514/811

[56] References Cited

U.S. PATENT DOCUMENTS

| | | | |
|---|---|---|---|
| 4,397,866 | 8/1983 | Wurtman | 429/319 |
| 4,405,629 | 9/1983 | Wurtman | 514/415 |
| 4,528,295 | 7/1985 | Tabakoff | 514/345 |
| 4,761,429 | 8/1988 | Blum | 514/561 |
| 5,559,152 | 9/1996 | Komissarova | 514/577 |

FOREIGN PATENT DOCUMENTS

| | | |
|---|---|---|
| 0342139 | 11/1989 | European Pat. Off. |
| 2607391 | 6/1988 | France |
| 61058560 | 5/1995 | Japan |
| 8002372 | 11/1980 | WIPO |
| 8904165 | 5/1989 | WIPO |
| 9313764 | 7/1993 | WIPO |
| 9504529 | 2/1995 | WIPO |

OTHER PUBLICATIONS

The Merck Index (11th Ed.), Budavari et al., Merck & Co., Inc., Rahway, N.J. (1989) pp. 894 and 952.

Dialog File: Derwent WPI, 004613843, WPI Acc. No.: 86–117187/18 (JP 61058560) 1986, Nippon Oils & Fats KK.

Komarek, L., Ceskoslovenska hygiene, vol. 34, No. 7–8, 1989, pp. 385–396.

Lehninger, A., Biochemistry, Moscow, MIR Publishing House, 1974, pp. 603–604.

Meister, A., Biochemistry of Amino Acids, Foreign Literature Publishing House, Moscow, 1961, pp. 64–65, 119–120.

Mashkovsky, M.D., Medicaments, New Wave Publishers, Moscow, 1996, pp. 12, 15, 52, 108, 121, 166–167.

*Primary Examiner*—Raymond Henley, III
*Assistant Examiner*—M. Moezie
*Attorney, Agent, or Firm*—Ladas & Parry

[57] ABSTRACT

A pharmaceutical composition having an antialcoholic and nootropic effect which is administered sublingually. The active ingredients of the composition are the amino acid L-threonine or a pharmaceutically acceptable salt thereof and vitamin $B_6$. A method for reducing and eliminating the pathological attraction to alcohol and treatment of alcohol abstinence syndrome, as well as a method for increasing attention comprises sublingual administration of an effective amount of the composition.

11 Claims, 2 Drawing Sheets

PHARMACEUTICAL COMPOSITION ENDOWED WITH AN ANTIALCOHOLIC AND NOOTROPIC EFFECT

This application is a 371 of PCT/RU96/00006 filed Jan. 4, 1996.

FIELD OF TECHNOLOGY

The present invention pertains to medicine, more particularly to a new pharmaceutical composition endowed with an antialcoholic and nootropic effect.

THE PRIOR ART

The problem of the search for and development of medicinal preparations for treatment of alcoholism remains pressing despite the active efforts of research workers in many countries of the world.

At the present time, a reduction in the use of alcohol is relatively easily achieved with preparations which to some degree produce an alcohol-like effect (tranquilizers, barbiturates, GOBA, antihistamine drugs with the tranquilizing effect). Such therapy, however, is known to lead to the development of toxicomanias significantly complicating the course of alcoholism, as well as reducing mental capacity. In treatment of alcoholism, the use of different psychotropic drugs and sensitizing drugs does not achieve the desired effect either, and, more than that, forms a markedly negative attitude to therapeutic measures.

In this connection, of special importance is the search for and development of new antialcoholic drugs having none of the above-mentioned shortcomings, reducing the pathological attraction and at the same time endowed with nootropic properties (increasing attention, improving memory, mental activity).

There are known preparations SAAVE™ and tropamine™ produced by Matrix Technologies, Inc. (J. of Psychoactive Drugs, vol. 20 (3), July–September 1988, p. 333). SAAVE™ is a combination of amino acids DL-phenylalanine, L-tryptophan, L-glutamine and purodoxal-5-phosphate and is recommended as a dietary supplement to the therapy for the subjects suffering from alcoholism and drug addiction (heroin, opiates, etc.). As compared with SAAVE, tropamine contains more additional substances and includes such amino acids as DL-phenylalanine, L-tyrosine, L-tryptophan, L-glutamine as well as pyridoxal-5-phosphate. It is also a dietary supplement in therapy for drug addicts.

Thus, both preparations are dietary supplements, that is, are used alongside with other therapeutic means and contain L-tryptophan the use of which in drugs and dietary supplements was forbidden by the FDA in 1989. Besides, these drugs have no nootropic effect.

The amino acid-containing mixtures are used for subjects abusing alcohol and suffering from alcololism or in the form of dietary supplements (international application WO 89/04165) or in the form of compositions (FR application No. 2607391) which comprise a full set of substitutable or unsubstitutable amino acids and additionally an abundance of most variable chemical compounds (sugars, polymeric carbohydrates, organic acids, fatty acids, phenol acids, phenol aldehydes, aspirin). In such mixtures, amino acids manifest no specific antialcoholic activity playing the; role of enteral nutrition, and, in the administration to man, are mainly used as a plastic material or the source of amino groups for the maintenance of nitric tissue balance. Certain attention should be paid to the compositions containing amino acid L-methionine in combination with vitamin $B_6$ (U.S. Pat. No. 4,528,295) and with L-alanine (international application WO 95/04529) employed, respectively, for decreasing the level of acetaldehyde in the blood and for the treatment of alcohol abstinence syndrome. However, the doses of amino acids and vitamin $B_6$ used in such mixtures exceed 5 to 10-fold the daily requirements which (as is well known) may entail significant disorders in protein and amino acid metabolism and additional marked changes in the vitamin balance and allergic complications. In some pathological conditions (U.S. Pat. Nos. 4,405,629; 4,397,866: international application WO 80/02372) amino acids may be used as precursors for increasing in the brain and the spinal cord the level of serotonin (L-tryptophan), adrenaline (L-phenylalanine and L-tyrosine) and glycine (L-threonine). But in these cases as well, very large doses thereof are used which may result in significant changes in the metabolism of biogenic amines and glycine in other elements of metabolism.

The analysis of the information pertaining to the medical application of amino acids shows that most frequently their property of correcting the nitric balance or their anabolic effect as food products are used.

Compositions of individual amino acids have found no medical application because of non-physiological amount of the dose (with the exception of SAAVE without L-tryptophan). This is indicated by the lack of the appropriate compositions in the nomenclature of drugs even in those countries which have the priority of invention.

DISCLOSURE OF THE INVENTION

The claimed composition is new and has not been described in the literature. The invention is based on the task of development of a new medicinal composition endowed simultaneously with an antialcoholic and nootropic effect, high activity, lacking toxicity and inducing no side-effects.

In accordance with this task there has been developed a composition comprising as the active ingredient the amino acid L-threonine and vitamin $B_6$ comprising a group of compounds—derivatives of 2-methyl-3-hydroxypyridine.

wherein R is $CH_2OH$, $CHO$, $CH_2NH_2$, R' is H, $PO(OH)_2$ threonine vitamers and coenzyme forms of $B_6$ vitamin.

The claimed composition is endowed with a highly effective antialcoholic and nootropic action and may be used for prevention and treatment of alcoholism (removal of pathologic attraction), detection of latent attraction for alcohol, and for increasing the mental capacity (increasing attention).

The preparation may be used in the form of tablets and powder. It is preferable to use it in the tablet form sublingually; one tablet contains 0.1–0.2 g L-threonine and 0.005–0.010 g vitamin $B_6$. Auxiliary substances for one tablet comprise 0.001–0.002 g methyl-cellulose and 0.001–0.002 g magnesium stearate.

The active ingredients of the preparation are obtained by: L-threonine- by microbiological or chemical synthesis, vitamin $B_6$ by chemical synthesis.

The active ingredients of the claimed composition comprise amino acid L-threonine and vitamin $B_6$. L-threonine (L-Thr, L-T) is a monoaminomonocarboxylic acid (L$\alpha$-amino-$\beta$-oxybutyric acid) which is an indispensable amino acid which is a part of all proteins with the exception of protamins. This is a crystalline substance soluble in water.

(1). $CH_3CH(OH)CH(NH_2)COOH$-I$\alpha$-amino-$\beta$-oxybutyric acid, L-threonine. Vitamin $B_6$ comprises a group of compounds, derivatives of 2-methyl-3-hydroxypyridine of the general formula:

(2)

In nature, there occur 3 forms (vitamers) of vitamin $B_6$ (formula 2):
pyridoxine (pyridoxile) wherein R is $CH_2OH$, R' is H;
pyridoxal wherein R is CHO, R' is H;
pyridoxamine wherein R is $CH_2NH_2$; R' is H.
They are all soluble in water and ethanol, and poorly soluble in other organic solvents.

Besides, the group of compounds endowed with the properties of vitamin $B_6$ comprises phosphoric ethers of vitamers (in formula 2, R' is $PO(OH)_2$) forming catalytically active (coenzymatic) forms of vitamin $B_6$: pyridoxine phosphate, pyridoxal phosphate, and pyridoxamine phosphate. These three compounds in a living organism easily transform into each other. The main coenzymatic form is pyridoxal phosphate which is a component of the active center of enzymes of nitric metabolism.

DETAILED DESCRIPTION OF THE INVENTION

Pharmacological effects of the claimed composition were investigated in persons of different age-groups. Its effect was tested in 12 apparently normal people of 30–40 years of age; 64 apparently normal teen-agers of 16–17 years with different neuro-psychic and emotional conditions, at different degrees of social adaptability; 544 patients with alcoholism of II–III degrees of 18–55 years of age (the control group—113 persons treated with neuroleptics, antidepressants, and tranquilizers).

The patients received the claimed composition in tablet form for sublingual administration containing 0.1–0.2 g of L-threonine, 0.005–0.01 g vitamin $B_6$, the binding and lubricating agents or in the powder form (sublingually) comprising L-threonine and vitamin $B_6$ in the same ratios.

In addition to the clinical evaluation, some patients were examined electroencephalographically and psycho-physiologically.

The results obtained permitted a conclusion that the claimed composition causes no side-effects and posesses the properties of:

1. stimulating cognitive processes, increasing attention and working capacity, reducing the signs of fatigue in apparently normal persons and in those suffering from alcoholism;
2. inducing reaction in persons with latent attraction to alcohol;
3. decreasing or completely eliminating pathological attraction to alcoholic drinks.

It was established that the claimed composition could be used without limitations in industrial enterprises where the production process demands rapid psycho-physiological reactions and turning attention from one thing to another. It has been shown that against the background of the use of the alleged composition the productivity of labor of the patients with alcoholism in the II–III degrees increased by 15–35%.

The results of the studies of the effect of the claimed composition are presented in examples I–VI.

EXAMPLE I

In a group of volunteers (average age 37.5 years, 9 men, 3 women; among them 8 physicians, 2 teachers, 1 psychologist, 1 journalist) the study was carried out in 2 stages at a 7-day interval. The results of the examinations were registered in a special protocol recording changes in the condition every 15 min. For the purpose of an objective evaluation, a dose of the composition was from 0.2–0.3 g to 0.6–0.7 g per one taking. The pharmaceutical composition was administered sublingually. The volunteers were observed for 4–5 hours.

The analysis of the results showed that the majority of the examinees within 10–15 min after administration of the pharmaceutical composition developed a feeling of general slackness, elimination of tension; at 15–25 min they developed the state of sedation, comfort, a desire for communication and exchange of opinions on the changes in their conditions. All the examinees noted the disappearance of constraint, feelings of awkwardness, shyness. At 45–75 min, they developed a state of freshness and desire to do some work.

In the majority of cases the claimed composition was administered in the afternoon when the examinees developed somnolence, unpleasant feeling of heavy head, general tiredness. The observations showed said conditions disappeared completely within 1½–2 hours, and the state of psychic and physical comform after taking the claimed composition persisted for another 4½–5 hours. Practically all the patients on that day had deep sleep, feeling of relaxation and satisfaction after waking.

Four examinees within 1½ hours after taking of the claimed composition felt an increased appetite. The analogous effect was observed in the second sate of the investigation one week later.

Three female volunteers for many years experienced manifestations of asthenic syndrome of unknown etiology with prevalence of increased fatigue, permanent feeling of being jaded, loss of appetite, headaches, sleep disorders. These patients were given the claimed composition in doses of 0.2 g 3 times daily for 3 weeks. All of them reported definite improvement of their conditions and better working capacity due to concentration of attention.

EXAMPLE II

In another category of examineers (64 teen-agers of 16–17 years, pupils, among them 46 boys and 18 girls) we studied the effect of the claimed composition on their feelings, emotional condition, psycho-physiological reactions, mental working capacity. Special tests of the programme of international complex examinations of adolescents INTERADOL (J. Komarek et al. 1989) were used for the evaluation of their neuro-psychic and emotional statuses, the degree of social adaptation and vegetative stability. Alongaside with these, we used questioning and visual observations, evaluation of the dynamics of emotional conditions using Lusher test, examinations of the dynamics of mental working capacity by means of the test for addition of 184 pairs of figures (Krepilin table), determination of the dynamics of the volume of short-time memory and attention (Schulte test), examinations of the pulse rate and arterial blood pressure.

All the adolescents were given the claimed composition in a dose of 0.2 g sublingually, all the examinations were done before and 30 min after the administration of the composition.

The claimed composition induced in 25% of cases (group I—the adolescents abusing alcohol and feeling attraction to it) marked vascular reactions (reddening of the skin of the face, hands, body, moderate sweating). The majority of the adolescents of this group felt mild dizziness, improved mood, evaluating this condition "like after drinking a glass of wine". This group of adolescents was characterized by the presence of astheno-neurotic derivations, chronic emotional stress, moderate and low level of social adaptation.

In 34% of the adolescents (group II) with neurotism and emotional instability after the administration of the claimed composition we observed definite improvement in the mood and development of self-assurance.

In 32% of the adolescents (group III) no response to the claimed composition was observed, and in 9% (group IV) the claimed composition caused "worsening of the mood" with a feeling of self discontent.

Group IV and especially group III consisted predominantly of the adolescents with the stable emotional status, lack of asthenovegetative disorders, high level of social adaptation.

The investigations of the effect of the claimed composition on the psycho-physiological function and metal working capacity showed (Table 1) the claimed composition to exert no effect on the short-time memory volume. At the same time it was established that the claimed composition exerts a marked positive effect on the attention function (Table 2). This effect practically does not depend on the pattern of response of the adolescents to the taking of the claimed composition in the above-mentioned groups (I–IV). In most of the teen-agers (particularly in groups I, II, and III) the time of changing of attention shortened by 1.5-fold or more with parallel decrease in the number of mistakes in performing Schulte's test. The rank correlation between the speed and accuracy of the work was most marked (r=0.52; r—correlation coefficient) in the teen-agers abusing alcohol (Group I), but these parameters were least interrelated in those who reported worsening of the mood in response to the administration of the claimed composition (group IV). Under the effect of the claimed composition also increased the rate of computation operations in the test of addition of 184 paired figures (before the administration of the composition 437.1±14 sec., after the administration 352.8±10.4 sec.; P 0.05 by Fischer criterion).

TABLE 1

The volume of short-time memory and the dynamics thereof in adolescents with different types of reaction to the claims composition

| The groups examined | Initial data | | | 30 min. after administration of the composition | | | |
|---|---|---|---|---|---|---|---|
| | M* | σ | m | M* | σ | m | P |
| Group I (16 adolescents) specific reaction | 49.3 | 12.799 | 3.305 | 37.0 | 13.375 | 4.230 | 0.05 |
| Group II (22 adolescents) improved mood | 44.6 | 13.465 | 4.768 | 49.3 | 13.87 | 3.581 | |
| Group III (20 adolescents) no changes | 37.1 | 12.044 | 3.219 | 41.1 | 18.333 | 6.111 | |
| Group IV (6 adolescents) worsening of mood | 33.3 | 15.055 | 6.146 | 45.0 | 13.78 | 5.627 | |

*The short-time memory was measured in %. M - arythmetic mean; σ - dispersion

TABLE 2

The characteristics of attention and dynamics thereof in adolescents with different type of response to the claimed composition (examinations of attention by means of schulte test)

| Groups examined | Values tested | Initial data | | | 30 min after administration of the composition | | | |
|---|---|---|---|---|---|---|---|---|
| 1 | 2 | M* 3 | σ 4 | m 5 | M* 6 | σ 7 | m 8 | P 9 |
| Group I (16 adolescents specific reaction | Total time of test performance | 421.3 | 88.64 | 22.88 | 302.9 | 82.97 | 23.01 | 0.01 |
| | Time of switching of attention | 142.6 | 52.94 | 13.67 | 83.8 | 38.17 | 10.50 | 0.05 |
| | No of mistakes | 6.2 | 5.87 | 1.51 | 2.0 | 3.18 | 0.88 | 0.05 |
| Group II 22 adolescents) | Total time of test perfor- | 378.2 | 79.99 | 20.65 | 297.3 | 53.28 | 13.75 | 0.01 |

TABLE 2-continued

The characteristics of attention and dynamics thereof in adolescents with different type of response to the claimed composition (examinations of attention by means of schulte test)

| Groups examined 1 | Values tested 2 | Initial data | | | 30 min after administration of the composition | | | |
|---|---|---|---|---|---|---|---|---|
| | | M* 3 | σ 4 | m 5 | M* 6 | σ 7 | m 8 | P 9 |
| improved mood | mance | | | | | | | |
| | Time of switching of attention | 137.8 | 50.29 | 12.98 | 85.9 | 46.88 | 12.10 | 0.01 |
| | No of mistakes | 5.3 | 3.95 | 1.02 | 2.5 | 3.06 | 0.79 | 0.05 |
| Group III (20 adolescents no changes) | Total time of test performance | 474.0 | 125.5 | 32.40 | 285.4 | 114.1 | 30.49 | 0.01 |
| | Time of switching of attention | 136.3 | 80.0 | 22.18 | 97.5 | 54.12 | 15.62 | 0.05 |
| | No mistakes | 4.7 | 3.28 | 0.84 | 2.0 | 1.91 | 0.53 | 0.05 |
| Group IV (6 adolescents) worsening of mood | Total time of test performance | 419.0 | 70.51 | 28.78 | 400.1 | 62.18 | 25.38 | |
| | Time of switching of attention | 145.5 | 43.81 | 17.88 | 137.00 | 42.76 | 17.46 | |
| | No mistakes | 6.6 | 2.80 | 1.14 | 2.8 | 1.32 | 0.54 | 0.05 |

*The time was recorded in seconds; errors in absolute values
M - arythmetic mean value;
σ - dispersion It was also established in the examined groups of adolescents that under the influence of the claimed composition the pulse rate in 40% of the examinees became lower (in the presence of initial tachycardia) and the systolic arterial blood pressure normalized (its initial raised values being in the range of 130–150 mm Hg).

EXAMPLE III

The effect of the claimed composition on the course of the alcohol abstinence syndrome (AAS) was studied in 481 patients. The clinical evaluation was done for the dynamics of the symptoms in scores, the results of electroencephalograms, and the rate of counting-computation operations.

The experimental (main) group of patients received the claimed composition according to the following schedule:
  on the first day 1–3 tablets per taking, three times daily (a single dose of 0.1–0.3 g, daily dose 0.3–0.9 g);
  from the 2nd day on, 1–2 tablets per taking, 3 times daily (a single dose of 0.1–0.2 g, the daily dose 0.3–0.6 g) for 3–4 weeks.

The tested composition was used in tablets and in the powder form 3 minutes before meals, sublingually (without drinking water).

This investigation evaluated:
  the dynamics of individual symptoms expressed in scores;
  integral evaluation of the condition by the sum of the scores;
  the degree of the influence of the claimed composition on the symptoms of the alcohol abstinence syndrome (AAS).

The severity and condition of the patients were evaluated by means of special cards for registration of the efficacy of a psychotropic drug and by glossary "Standard psychopathological symptoms and syndromes for consistent clinical evaluation of alcoholism and alcoholic psychoses" (M., 1976). The patients were examined before the beginning of the therapy and at 1,3,7,10,14, 21, and 28 days after that.

In the majority of the patients, AAS (severe and moderately severe) was very extensive comprising somatic, neurological and psychopathological disorders.

The results of the study revealed a positive effect of the claimed composition in the overwhelming majority of the patients (Tables 3 and 4).

TABLE 3

Integral evaluation of the dynamics of the abstinence signs in the main and control groups (the combination of signs "anxiety, tremor, tachycardia, etc")

(M - arythmetic mean in scores; σ - dispersion in scores)

| Day of therapy | 1 | | 3 | | 7 | | 10 | |
|---|---|---|---|---|---|---|---|---|
| Group | M | σ | M | σ | M | σ | M | σ |
| Patients | 0.52 | 0.51 | 0.47 | 0.51 | 0.00 | 0.00 | 0.04 | 0.20 |
| Controls | 0.48 | 0.51 | 0.42 | 0.51 | 0.47 | 0.51 | 0.23 | 0.43 |
| Significance of differences | 0.26 | | 0.29 | | 3.92 | | 2.04 | |
| | | | | | $P < 0.001$ | | $P < 0.01$ | |

| Day of therapy | 14 | | 21 | | 28 | |
|---|---|---|---|---|---|---|
| Group | M | σ | M | σ | M | σ |
| Patients | 0.05 | 0.23 | 0.04 | 0.20 | 0.04 | 0.20 |
| Controls | 0.26 | 0.45 | 0.19 | 0.40 | 0.12 | 0.33 |
| Significance of differences | 1.86 | | 1.71 | | 1.06 | |
| | $P < 0.01$ | | $P < 0.01$ | | $P < 0.05$ | |

TABLE 4

Integral evaluation of the condition of the patients of both groups (the combination of signs "therapeutic aims, attitude to the working activity, communicability, etc")
(M - arythmetic mean in scores; σ - dispersion in scores)

| Day of therapy | 1 | | 3 | | 7 | | 10 | |
|---|---|---|---|---|---|---|---|---|
| Group | M | σ | M | σ | M | σ | M | σ |
| Patients | 0.04 | 0.20 | 0.10 | 0.30 | 0.53 | 0.51 | 0.54 | 0.51 |
| Controls | 0.04 | 0.20 | 0.05 | 0.22 | 0.16 | 0.37 | 0.15 | 0.37 |
| Significance of differences | 0.00 | | 0.54 | | 2.52 $P < 0.01$ | | 3.16 $P < 0.01$ | |

| Day of therapy | 14 | | 21 | | 23 | |
|---|---|---|---|---|---|---|
| Group | M | σ | M | σ | M | σ |
| Patients | 0.69 | 0.48 | 0.74 | 0.45 | 0.79 | 0.42 |
| Controls | 0.16 | 0.37 | 0.23 | 0.43 | 0.58 | 0.51 |
| Significance of differences | 3.81 $P < 0.001$ | | 4.16 $P < 0.001$ | | 1.37 $P < 0.05$ | |

Figure 1:
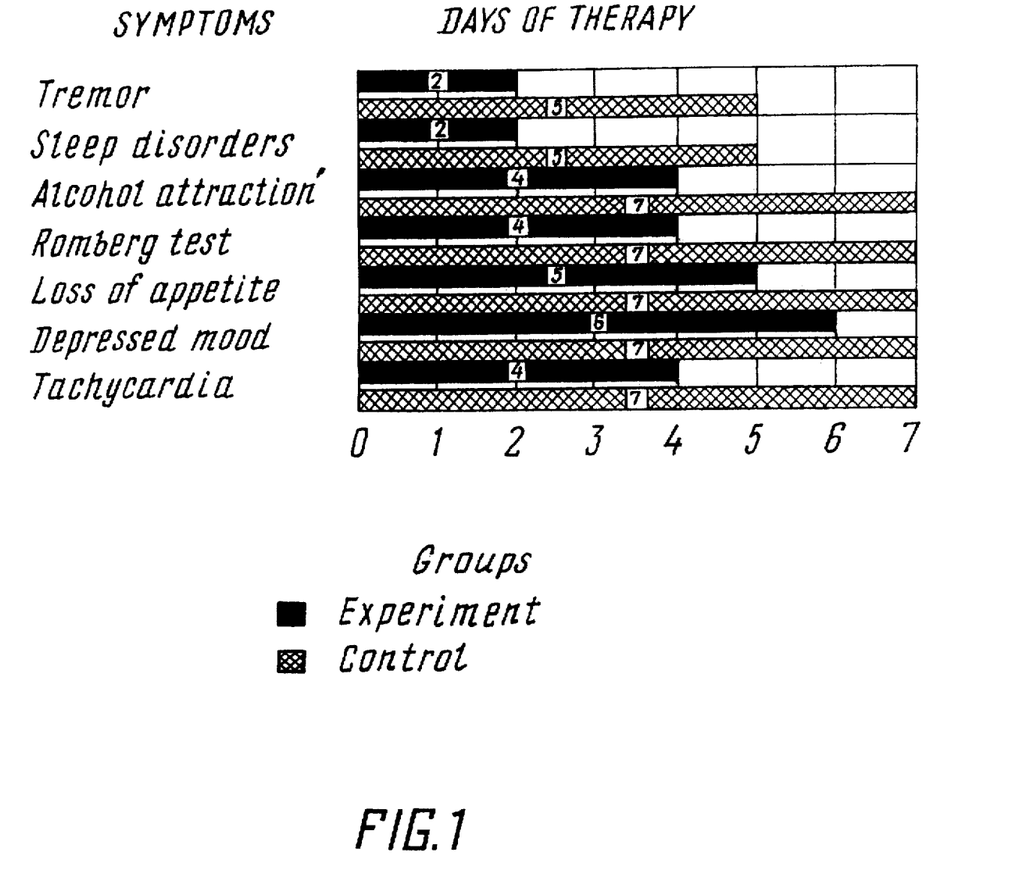
FIG. 1 Time of disappearance of AAS symptoms in experimental and control groups.
AAS - alcohol abstinence syndrome;
O - experiment; K- control.

During the course of therapy, immediately after taking the claimed composition, the patients experienced mild relaxation with a feeling of pleasant warmth in the body, however, during the day the patients were cheerful, full of energy. Beginning from the 2nd–5th day after taking the claimed composition, the patients experienced weakening of anxiety, worry, decrease of the emotional stress, irritability, depressive mood, and feeling of guilt. The sleep and appetite normalized, three appeared positive emotions, sense of humor. The moods stabilized and improved in combination with increasing general activity (FIG. 1).

The degree of the influence of the claimed composition on AAS symptoms is shown in Table 5. The obtained results demonstrate that the effect is detectable as early as the first day and persists to 7th–10th day, but the degree of the claimed composition effect depends on the nature of the pathologic disorders. The effect of the composition is less pronounced in the dynamics of neurological disorders and astheno-vegetative disturbances.

TABLE 5

AAS structure and the effect thereon of the claimed composition

| N AAS | | Days | | | | | | |
|---|---|---|---|---|---|---|---|---|
| 1 | 2 | 1 3 | 2 4 | 3 5 | 4 6 | 5 7 | 6 8 | 7 9 |
| 1 | Attraction to alcohol | ++ | ++ | ++ | ++ | ++ | ++ | +++ |
| 2 | Motor anxiety | ++ | ++ | ++ | ++ | ++ | ++ | ++ |
| 3 | Agitation, stress | ++ | +++ | +++ | +++ | +++ | +++ | +++ |
| 4 | Anxiety, fear | ++ | +++ | +++ | +++ | +++ | +++ | +++ |
| 5 | Depression, Suicidal thoughts | ++ | ++ | +++ | +++ | +++ | +++ | +++ |
| 6 | Affective lability, tears | +++ | +++ | +++ | +++ | +++ | +++ | +++ |
| 7 | Ideas of guilt, relations | ++ | ++ | ++ | +++ | +++ | +++ | |
| 8 | Emaciation, asthenia | +++ | +++ | +++ | +++ | +++ | +++ | |
| 9 | Sluggishness, depression | +++ | +++ | +++ | +++ | +++ | +++ | |
| 10 | Disorders in falling asleep | ++ | ++ | +++ | ++ | +++ | +++ | |
| 11 | Interrupted sleep | ++ | ++ | ++ | +++ | +++ | +++ | |
| 12 | Early waking up | ++ | ++ | ++ | +++ | +++ | +++ | |
| 13 | Irritability, dysphoria | ++ | +++ | +++ | +++ | +++ | +++ | |
| 14 | Weakness, asthenia | +++ | +++ | +++ | +++ | +++ | +++ | |
| 15 | Sweating, palpitation | + | + | + | ++ | ++ | ++ | |
| 16 | Cardiac rhythm disorders | + | + | + | ++ | ++ | ++ | |
| 17 | Thirst, xerostomia | ++ | ++ | ++ | ++ | ++ | ++ | |
| 18 | Headaches, dizziness | ++ | ++ | ++ | ++ | ++ | ++ | |
| 19 | Intention tremor | + | + | + | ++ | ++ | | |
| 20 | Dyspnea | ++ | ++ | ++ | ++ | | | |
| 21 | Gastro-intestinal disorders | ++ | +++ | +++ | +++ | +++ | +++ | |

Evaluations: O - no effect, + - weak effect, ++ - moderate effect, +++ - marked effect By the 7th day of therapy, statistically significant differences between the main and control groups appeared in such signs as the attitude to personal appearance, working activity, family (Table 4). In the same period increased activity without motor and will disinhibition were observed.

The values of the criteria "critical attitude" and "therapeutic aims" were characterized by lower dynamics, however, their changes in the group of the patients given the claimed composition were greater than in the controls. In a long course administration of the claimed composition (2–3 months) a marked aim for therapy was observed.

The influence of the claimed composition on the electric activity of the brain in AAS was investigated. The study was carried out in two stages. In the first stage, EEG was analysed for 2 hours after a single taking of 0.3 g of the claimed composition. In the second stage, the EEG parameters were registered in the process of the course treatment. After registration of the background bioelectric activity, the patient received the pharmacological composition or placebo followed by continuous registration and analysis of EEG for 20 min. Subsequently, the registrations were made 60, 90, 120 and 240 min after taking of the composition.

During the course therapy, the registration and analysis of the background EEG were done once a week.

The analysis was done on artefact-free areas of EEG of 1 min . 45 sec. duration.

In the statistical treatment, the arythmetic mean and dispersion (σ) were calculated for the values of relative powers of the rhythm in five ranges (see Tables 6–8), as well as the total spectral power of EEG. Then the resulting values were subjected to logarithmic transformation consisting in calculating the calculation of natural logarithms of the initial values. The purpose of this mathematical procedure consisted in the approximation of the primary data to the normal distribution criteria. The results of the investigations are presented in Tables 6–8 and in FIG. 2.

TABLE 6

Changes in the spectral parameters of EEG under the influence of the claimed composition during 20 min after administration thereof (for placebo the level is taken for 0)

| Interval of testing (min) | Frequency ranges (Hz) | | | | | |
|---|---|---|---|---|---|---|
| | Δ 0.5–4.0 | | Θ 4.0–8.0 | | α 8.0–13.0 | |
| | RL | LL | RL | LL | RL | LL |
| 0.0–3.5 | 0.08 | −0.31 | 0.07 | −0.06 | 0.04 | 0.08 |
| 3.5–7.0 | −0.47 | **−0.62 | 0.03 | −0.09 | 0.11 | 0.04 |
| 7.0–10.5 | *−0.69 | ***0.70 | 0 | −0.11 | 0.14 | 0.03 |
| 10.5–14.0 | *−0.59 | **−0.52 | 0.01 | −0.01 | *0.14 | 0.12 |
| 14.0–17.0 | **−0.90 | *−0.52 | 0.04 | −0.07 | *0.13 | 0.06 |
| 17.0–20.5 | **−0.87 | −0.43 | 0.05 | −0.01 | *0.18 | 0.06 |

| Interval of testing (min) | Frequency ranges (Hz) | | | | EEG summary power |
|---|---|---|---|---|---|
| | β₁ | | β₂ | | |
| | RL | LL | RL | LL | |
| 0.0–3.5 | −0.05 | 0.02 | −0.02 | 0.05 | 0.10 |
| 3.5–7.0 | 0.02 | 0.04 | 0.05 | 0.05 | 0 |
| 7.0–10.5 | 0 | 0.03 | 0.03 | 0.09 | 0.11 |
| 10.5–14.0 | −0.03 | 0 | 0.01 | 0.05 | **0.26 |
| 14.0–17.0 | −0.07 | −0.02 | −0.02 | 0.06 | **0.29 |
| 17.0–20.5 | 0.03 | 0.01 | 0.01 | 0.03 | **0.36 |

RL - lead from the right hemisphere; LL- lead from the left hemisphere
The significance of differences:
*p < 0.05
**p < 0.01
***p < 0.001

TABLE 7

The dynamics of EEG spectral parameters during 2 hours after the administration of the claimed composition (for placebo, the level is taken for 0)

| Stage of examination (min) | Frequency ranges (Hz) | | | | | |
|---|---|---|---|---|---|---|
| | Δ 0.5–4.0 | | Θ 4.0–8.0 | | α 8.0–13.0 | |
| | RL | LL | RL | LL | RL | LL |
| 45 | ***−1.23 | ***−1.46 | −0.21 | −0.19 | 0.20 | *0.25 |
| 60 | **−0.77 | ***−1.29 | −0.10 | *−0.13 | *0.13 | **0.18 |
| 90 | ***−0.98 | ***−1.32 | **−0.14 | **−0.12 | 0.01 | **0.14 |
| 120 | ***−1.16 | ***−1.43 | −0.13 | **−0.18 | 0.07 | 0.11 |

| Stage of examination (min) | Frequency ranges (Hz) | | | | EEG summary power |
|---|---|---|---|---|---|
| | β₁ 13.0–20.0 | | β₂ 20.0–32.0 | | |
| | RL | LL | RL | LL | |
| 45 | **−0.10 | ***−0.15 | −0.03 | *−0.10 | 0.27 |
| 60 | 0 | −0.01 | 0.03 | 0.01 | 0.10 |
| 90 | 0 | 0.02 | 0.04 | 0.04 | 0.02 |
| 120 | −0.03 | −0.01 | 0.04 | 0.01 | *0.11 |

RL - lead from the right hemisphere; LL-lead from the left hemisphere
The significance of differences:
*p < 0.05
**p < 0.01
***p < 0.001

TABLE 8

Comparative characteristics of changes in EEG frequency ranges in the main and control groups during the course therapy (the values for the right and left leans are summarized)

| Week of therapy | Frequency ranges (Hz) | | | | | |
|---|---|---|---|---|---|---|
| | Δ 0.5–4.0 | | Θ 4.0–8.0 | | α 8.0–13.0 | |
| | M | C | M | C | M | C |
| 0 | 2.9 | 2.7 | 3.6 | 3.5 | 7.4 | 7.2 |
| 1 | **1.3 | 2.2 | *2.8 | 3.1 | **9.1 | 7.9 |
| 2 | *1.1 | 1.4 | 1.9 | 1.7 | *9.4 | 8.6 |
| 3 | 1.4 | 1.2 | 1.8 | 1.8 | 8.9 | 9.1 |
| 4 | 1.3 | 1.1 | 1.8 | 1.8 | 8.7 | 9.0 |

| Week of therapy | Frequency ranges (Hz) | | | | Summary power | |
|---|---|---|---|---|---|---|
| | β₁ 13.0–20.0 | | β₂ 20.0–32.0 | | | |
| | M | C | M | C | M | C |
| 0 | 6.4 | 6.4 | 7.5 | 7.7 | 2.6 | 2.3 |
| 1 | 7.1 | 6.5 | 8.0 | 7.9 | **3.4 | 2.1 |
| 2 | 7.8 | 7.5 | 8.2 | 8.1 | *2.9 | 2.1 |
| 3 | 8.1 | 7.8 | 8.8 | 8.6 | 2.9 | 3.2 |
| 4 | 7.9 | 7.8 | 8.6 | 8.6 | 2.9 | 3.1 |

M - the main group, C - control group
The significance of differences: *P < 0.05; **P < 0.01

Table 6 presents the mean logarithmic values of the relative EEG power by frequency ranges, as well as total spectral power during the first 20 min after taking the claimed composition and placebo (the placebo level is taken as zero (0)).

The examinations showed that significant changes were observed as early as 3 minutes after administration of the claimed composition and were manifested in the increasing inhibition of the slow-wave activity of the delta-range in combination with increasing power of the alpha-rhythm and total spectral power of EEG, the increase of the latter values against the background of taking of the composition reaching significant values from the 10th minute of examinations.

The further analysis of the EEG changes (Table 7) shows the trends to persist for two hours after a single administration of the claimed composition, although by the end of the examination there is some decrease in the alpha rhythm in the lead from the right hemisphere.

The dynamics of mean logarithmic values of relative power in the spectrum ranges in the main and control groups during the 4-week course therapy is presented in Table 8. It may be seen that the significant differences between the groups manifested, as before, in a decrease in the power of slow (delta and theta) rhythms and increase in the alpha activity in combination with an increase in the total power of EEG persisted for the first two weeks and subsequently smooth down due to an increase in the corresponding values in the control group.

Figure 2:
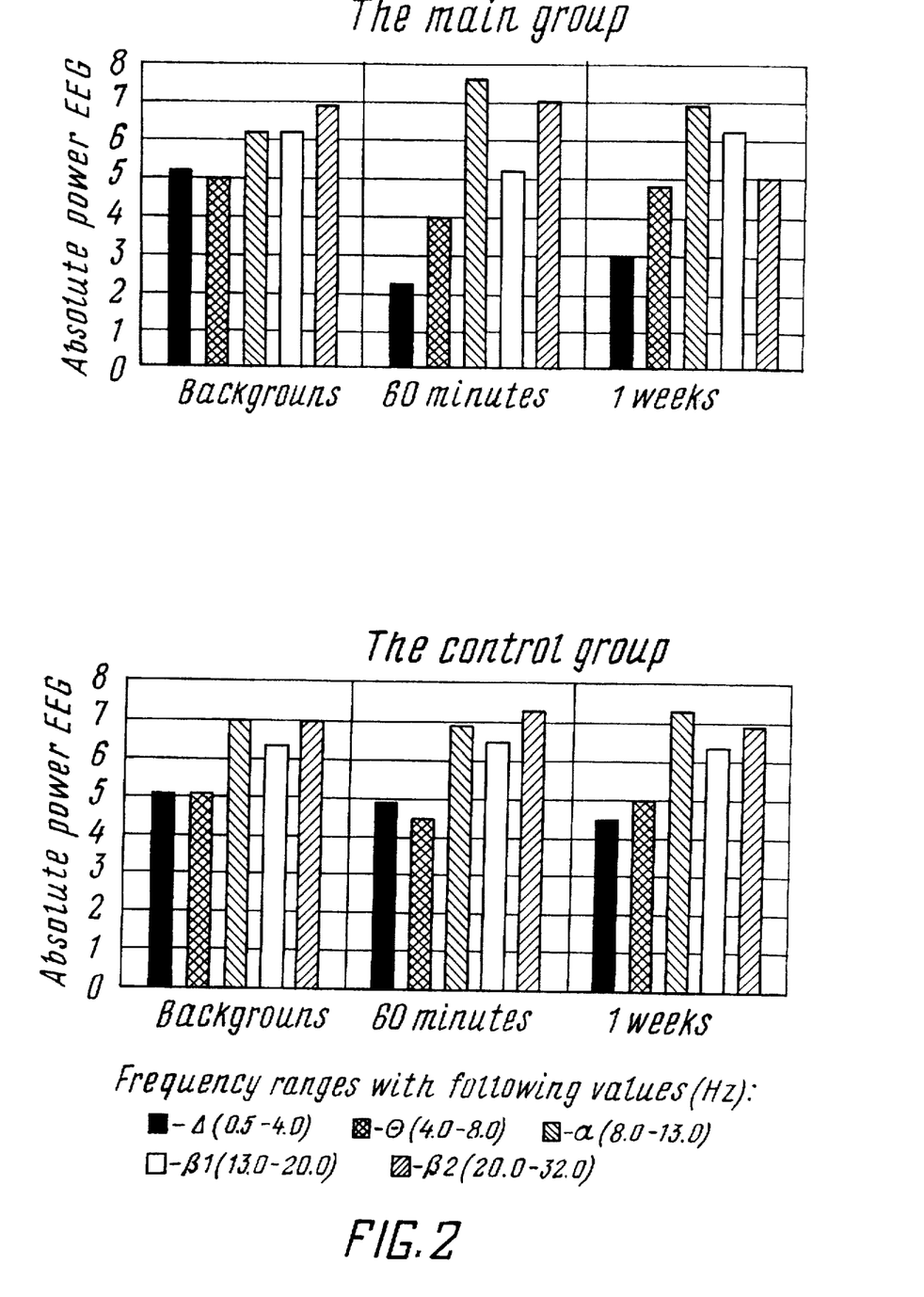
FIG. 2 The dynamics of mean values of absolute power in frequency ranges of EEG in the experimental and control groups at different stages of the test. On the abscissa—observation time, on the ordinate—absolute power of the EEG spectra; $\Delta$, $\theta$, $\alpha$, $\beta_1$, $\beta_2$— frequency ranges with the following values, Hz:0.5–4.0 ($\Delta$); 4.0–8.0 ($\theta$); 8.0–13.0 ($\alpha$); 13.0–20.0 ($\beta_1$); 20.0–32.0 ($\beta_2$).

A comparative analysis of changes in the spectral characteristics of EEG under the influence of the claimed composition and placebo is illustrated in FIG. 2 showing the initial values of the absolute power in spectral ranges as well as changes thereof 60 min after a single dose of 0.3 g of the composition and at 7 days after the beginning of the course therapy.

It will be seen in FIG. 2 that under the influence of the claimed composition there occurred a rapid normalization of the EEG spectral parameters which apparently is associated with the stimulating effect of the composition on the bioenergetic processes in the brain cells. In the control group of the patients given placebo the dynamics of the EEG spectral characteristics is much less marked.

In the course of the trials, the pharmaco-EEG properties of the claimed composition were compared with the properties of the main psychotropic drugs. The results of the comparison permit to assign this composition to psychopharmacological drugs endowed with the stimulating effect on the cognitive processes.

The effect of the claimed composition on the rate of the count-computational operations performed by the subject suffering from alcoholism receiving a 7–10-day course of treatment with said composition. The test consisted in summing up 184 pairs of figures. The time of performing the task and the number of mistakes were recorded.

The investigations showed that after many administrations of the claimed composition, as early as the 3rd–5th day from the start of the treatment there was a trend for an increase in the rate of performance of the task. From the 7th–10th day there was a statistically significant increase in the rate of performance of the counting-computational operations which was not disturbed in the long-term course of the composition administration.

EXAMPLE IV

The influence of the claimed composition on attraction to alcohol was studied. The observations involved 180 patients suffering from chronic alcoholism of the 2nd stage. The age of the patients varied from 18 to 65 years, and duration of the disease from 3 to 20 years, the duration of the drinking period from 2 to 20 days; the extent of the attraction in scores was from 4 to 7.

The majority of the patients stated the lack of independent suppression of alcohol attraction.

Clinical observations permitted to differentiate several variants of enhancement of alcohol attraction. Most frequently (variant I) alcohol attraction was accompanied by affective disorders: unstable moods, increased irritability, pessimism, resentment, unreasonable alarm, tenseness, want of faith in personal capacities, despair, sleep disorders. In the majority of cases these manifestations were accompanied by vegetative disorders: sweating, hypertension, thirst, tremor, vasoconstriction, vasodilation.

Some patients had sensory and mental variant (variant II) of enhancement of alcohol attraction. In this group, the patients complained of permanent unpleasant feelings in the stomach comparable to the feeling of hunger, increased salivation, thirst, break down, general weakness, asthenia, depressed mood. These symptoms were always accompanied by "thinking of alcohol".

In the third group of the patients (variant III), phenomena of physical discomfort were predominant in the structure of pathological attraction. The fourth group (Variant IV) was characterized by marked behaviourial disorders.

In these groups the claimed composition was administered sublingually, 0.1–0.3 g per taking for 4–5 days without administration of psychotropic drugs.

The analysis of the results showed that the highest efficacy of the claimed composition was observed in the patients with affective disorders (variant I) or in those with the combination of the sensory (hunger) and mental (thoughts of alcohol) (Variant II) components in the structure of the pathological attraction. In the first group of the patients, the administration of the claimed composition decreased the frequency of such manifestations as excessive resentment, alarm, irritability, tenseness; their sleep improved, they became more confident in their capacities, noted significant improvement in their physical condition, did not think their treatment was hopeless, their moods improved and became more stable. After the first course of the therapy the patients were given 3–6 more courses of 4–5 days during one year. In all the cases, after the repeat courses the patients noted the positive effect of the claimed composition on the abovementioned symptoms. During these course treatments only in 8% of the cases "a derangement" (a single taking of alcohol) was accompanied by the development of relapse.

When the composition was given to the patients of the second group (prevalence of sensory and mental components), as early as within 30–60 min. after administration the patients noted improvements in their conditions: decreased weakness and asthenia, the thoughts of alcohol "disappeared somewhere", they felt general slackness and quieting down, very frequently definite feeling of hunger appeared—they wanted "abundant and delicious food". Satisfying the hunger with good food gave the feeling of physical and psychic comfort, and in some cases—deep sleep. In this group of patients also only in 8% of the cases "a derangement" was accompanied by the development of relapse of this disease.

A less marked effect of the claimed composition was observed in the patients in whose pathological attraction structure the phenomena of physical discomfort were predominant (group 3). Nevertheless, during the treatment period the patients noted the improvement evaluating their condition as "quiet".

In those cases where behaviourial disorders were prevalent in the structure of enhanced pathological attraction to alcohol (variant IV), the claimed composition was of low effect and psychotropic drugs had to be used.

EXAMPLE V

The effect of the claimed composition on attraction to alcohol was studied by the double-blind control method. The conditions of the patients were evaluated by two examiners independently. The third examiner randomly prescribed to the patients the claimed composition or placebo. A preparation of rhytin (inositolhexaphosphoric acid). Within three days the preparation for the patient was changed for the opposite one. At the end of three treatment period the data obtained by the two examiners were compared, after which the data on the order of the administration of the preparations were disclosed.

The average age in this group of patients was $34.0 \pm 1.8$ years (from 26 to 43 years), the average duration of the disease $7.7 \pm 1.7$ years (from 3 to 20 years), the duration of the drinking periods $5.6 \pm 2.2$ days (from 2 to 14 days), the extent of attraction $5.8 \pm 0.28$ scores (from 4 to 7).

Most patients stated that, upon the appearance of attraction to alcohol the fight for abstention continued for several hours, in two patients—for several days. All the patients declared that they could not independently suppress the attraction to alcohol. At the time of examination, in 70% of the cases the attraction to alcohol was manifested in affective disorders. They comprised complaints of irritability, gloomy-melancholy mood, inner stress, the feeling of lacking something. All the patients associated their poor condition with the lack of possibility to use alcohol. In 20% of the cases the patients observed the feeling of attraction appearing with the feeling of hunger.

The patients who first were given placebo felt no effect for the first 2–3 days. By the 3rd day attraction to alcohol disappeared in all the patients. The change from placebo to the claimed composition they did not feel.

When the claimed composition was given first, in some patients (30%) the attraction to alcohol disappeared already after the first taking of the composition, in the remaining 70%—by the 2nd–3rd day.

The differences in the evaluation of the patients' conditions (including different manifestations of attraction to alcohol) by the two experts were insignificant. In 10% of cases only, the physicians did not recognize what the patient had been given: the claimed composition or placebo.

The clinicians concluded that the use of the double-blind control method revealed a high efficacy of the claimed composition as a preparation interrupting attraction to alcohol.

EXAMPLE VI

The results of clinical observations, psychophysiological and electrophysiological observations showed that the claimed composition, in addition to the anti-alcohol effect, is endowed with the nootropic effect: it increases the attention and the rate of counting-computation operations. These properties permitted to recommend the claimed composition for the treatment of patients with alcoholism working in industries requiring increased attention and rapid psychophysiological reactions (actions). For the confirmation of this proposition, the effect of the claimed composition was investigated in subjects of 25–60 years of age suffering from alcoholism of the II–III stage (the duration of alcohol use 10–30 years) working in industrial production. The studies were carried out in 50 patients treated in a day time hospital attached to a mechanical plant. The patients were given the claimed composition in a dose of 0.1 g 3 times daily for 2–3 months. The records included the clinical condition of the patients, their labor productivity, fatiguability, traumatism. The controls were 28 patients treated in the hospital. Both groups worked in a stamping shop making small details. This kind of work requires increased attention and rapid changing from one kind of work to another.

The observations showed that the incidence of traumas (finger damages) decreased in those workers who were given the composition, the patients subjectively observed less fatigueability by the end of the working shift. The productivity of labor increased by 15%–30% in those taking the composition.

Thus, the studies demonstrated that the claimed composition given for short and long periods of time is effective in increasing attention, mental working capacity, the speed of psycho-physiological reactions in any kinds of activity, may be used by healthy subjects and people suffering from alcoholism under conditions of industrial production requiring enhanced psycho-motor reactions.

The results of the investigations demonstrated that in the longterm administration the claimed composition is not habit-forming, causes no allergic reactions or other pathological complication.

INDUSTRIAL APPLICABILITY

The claimed composition endowed with an anti-alcoholic and a nootropic action can find application:

1. In pediatric and adult practice in cases of: decreased mental working capacity accompanied by attention disorders, in encephalopathies of different origin; and
2. in narcology for patients with alcoholism for prevention of the disease relapses, for reduction and elimination of pathological attraction to alcohol, and for treatment of alcohol abstinence syndrome.

We claim:

1. A pharmaceutical composition having an antialcoholic and nootropic affect consisting essentially of as active ingredients a mixture of the amino acid L-threonine or a pharmaceutically acceptable salt thereof and vitamin $B_6$ in therapeutically effective amounts and a pharmaceutically acceptable solvent, diluent or carrier said composition formulated for sublingual administration.

2. A pharmaceutical composition as claimed in claim 1 wherein the amino acid L-threonine or a pharmaceutically acceptable salt thereof and vitamin $B_6$ are in a weight ratio of (10–20):(0.5–1), respectively.

3. A pharmaceutical composition as claimed in claim 2 wherein the amino acid L-threonine or a pharmaceutically acceptable salt thereof and vitamin $B_6$ are in a weight ratio of 20:1.

4. A pharmaceutical composition as claimed in claim 1 in the form of a powder.

5. A pharmaceutical composition as claimed in claim 1 in the form of a tablet.

6. A pharmaceutical composition having an antialcoholic and nootropic effect consisting essentially of as active ingredients a mixture of the amino acid L-threonine or pharmaceutically acceptable salts thereof and Vitamin $B_6$ in therapeutically effective amounts, methylcellulose, magnesium stearate and a pharmaceutically acceptable solvent, diluent or carrier said composition formulated for sublingual administration.

7. A pharmaceutical composition as claimed in claim 6 wherein the ingredients are present in the following amounts (g):

| | |
|---|---|
| L-threonine or pharmaceutically acceptable [salts] salt thereof | 0.1–0.2 |
| Vitamin $B_6$ | 0.005–0.010 |
| methylcellulose | 0.001–0.002 and |
| magnesium stearate | 0.001–0.002. |

8. A method for reducing and eliminating pathological attraction to alcohol and for treatment of alcohol abstinence syndrome comprising administering sublingually to a mammal in need thereof the pharmaceutical composition as claimed in claim 1 in a therapeutically effective amount.

9. A method as claimed in claim 8 wherein said composition is administered in a dose of 1.5–4 mg/kg body weight.

10. A method for increasing attention comprising administering sublingually to a mammal in need thereof the pharmaceutical composition as claimed in claim 1 in a therapeutically effective amount.

11. A method as claimed in claim 10 wherein said composition is administered in a dose of 1.5–4 mg/kg body weight.

* * * * *